(12) United States Patent
Negron

(10) Patent No.: US 7,434,691 B2
(45) Date of Patent: Oct. 14, 2008

(54) INGESTIBLE CAPSULE PACKAGING

(75) Inventor: Laura A. Negron, West Seneca, NY (US)

(73) Assignee: The SmartPill Corporation, Buffalo, NY (US)

( * ) Notice: Subject to any disclaimer, the term of this patent is extended or adjusted under 35 U.S.C. 154(b) by 216 days.

(21) Appl. No.: 11/517,965

(22) Filed: Sep. 8, 2006

(65) Prior Publication Data
US 2008/0060952 A1 Mar. 13, 2008

(51) Int. Cl.
*B65D 83/04* (2006.01)
(52) U.S. Cl. .................. 206/530; 206/528
(58) Field of Classification Search ............. 206/459.1, 206/205, 210, 534, 539, 528, 530; 600/7, 600/109, 114; 348/77
See application file for complete search history.

(56) References Cited

U.S. PATENT DOCUMENTS

| 7,295,226 | B1* | 11/2007 | Meron et al. | 348/77 |
| 2006/0114086 | A1* | 6/2006 | Grigorov | 335/151 |
| 2007/0270641 | A1* | 11/2007 | Kimoto et al. | 600/109 |
| 2008/0027267 | A1* | 1/2008 | Segawa | 600/7 |
| 2008/0033243 | A1* | 2/2008 | Meron et al. | 600/109 |
| 2008/0039675 | A1* | 2/2008 | Segawa | 600/7 |

* cited by examiner

*Primary Examiner*—David T Fidei
(74) *Attorney, Agent, or Firm*—Phillips Lytle LLP

(57) ABSTRACT

A packaging system (15) for an ingestible capsule comprising an ingestible capsule (20) having a pH sensor (22) and an outer surface (24), packaging (16) for the capsule comprising an open well (28) having an inner surface (46-49) and a holding volume (33) defined by the inner surface of the well and the outer surface of the capsule, the inner surface of the well configured and arranged to engage at least a portion (25) of the outer surface of the well, and the holding volume configured to and arranged to contain a pH calibration fluid and to hold the pH sensor submerged in the pH calibration fluid when the pH calibration fluid is added to the well, whereby the packaging provides for calibrating the pH sensor without removing the capsule from the packaging. Activation system for an ingestible capsule comprising an ingestible capsule, a magnetic capsule activation unit (21) having an activation port (60), packaging for the capsule, the packaging comprising an open well having an inner surface and an outer surface (54-57), the inner surface configured to engage at least a portion of the ingestible capsule, the outer surface configured for seating in the activation port of the magnetic activation unit, whereby the capsule may be activated without removing the capsule from the packaging.

22 Claims, 13 Drawing Sheets

INGESTIBLE CAPSULE PACKAGING

TECHNICAL FIELD

The present invention relates generally to ingestible capsules and, more particularly, to packaging for an ingestible capsule which provides calibration and activation functionality.

BACKGROUND ART

Ingestible capsules are well-known in the prior art. Such capsules are generally small pill-like devices that can be ingested or swallowed by a patient. It is known that such capsules may include one or more sensors for determining physiological parameters of the gastrointestinal tract, such as sensors for detecting temperature, pH, pressure and the like.

It is also known that capsules may be activated by removing the packaging from the capsule and either inserting a battery into the capsule or manually turning the capsule on. Alternatively, it is known that a magnetic latch may be used to control the activation of the capsule. Such a latch will disconnect an electrical circuit in the presence of a magnetic field. With this arrangement, the capsule is packaged with a permanent magnet and, while the capsule is in the packaging, the latch is held in an inactive disconnected state by the enclosed magnet. When the capsule is removed from the packaging and separated from the magnetic field, the latch closes and connect the battery, thereby activating the capsule. This type of arrangement has a number of drawbacks such as cost, weight and size because a permanent magnet must be included in the packaging.

It is also known that capsules having pH sensors may be calibrated by removing the capsule from the packaging and placing it in a separate container of solution with a known pH. For example, it is know that a capsule may be calibrated with a dedicated calibration unit that contains several vials of buffer solutions at known pH levels. Calibration is performed by filling the vials with the appropriate solutions. An activated capsule is then placed in the first vial and the separate calibration unit is turned on. The calibration unit then prompts the user to move the capsule from vial to vial as the capsule is calibrated with each solution. However, such methods of calibration have a number of drawbacks such as inefficiency, risk of contamination, and lack of standardization.

Thus, there is a need for capsule packaging that allows for standardized calibration of sensors on the capsule, that limits the risk of contamination, and that allows for activation of the capsule at the desired time.

DISCLOSURE OF THE INVENTION

With parenthetical reference to the corresponding parts, portions or surfaces of the disclosed embodiment, merely for the purposes of illustration and not by way of limitation, the present invention provides an improved packaging system (15) for an ingestible capsule comprising an ingestible capsule (20) having a pH sensor (22) and an outer surface (24), packaging (16) for the capsule comprising an open well (28) having an inner surface (46-49) and a holding volume (33) defined by the inner surface of the well and the outer surface of the capsule, the inner surface of the well configured and arranged to engage at least a portion (25) of the outer surface of the well, and the holding volume configured to and arranged to contain a pH calibration fluid and to hold the pH sensor submerged in the pH calibration fluid when the pH calibration fluid is added to the well, whereby the packaging provides for calibrating the pH sensor without removing the capsule from the packaging.

The inner surface may be configured to engage at least a portion of the capsule by being sized such that least a portion of the capsule (25) fits snuggly into the well, and the inner surface may be configured to receive and releasably hold the capsule by friction. The inner surface of the well may comprise a substantially cylindrical portion (48), the outer surface of the capsule may comprise a substantially cylindrical portion (25), and the well portion may have a diameter that is slightly greater than the diameter of the capsule portion.

The system may further comprise an open recess (34) configured to receive calibration fluid and communicating with the well such that calibration fluid poured into the recess is communicated to the holding volume. The recess and the well may communicate by at least one channel (35) between the opening of the recess and the opening of the well. The channel may be U-shaped. The holding volume may be configured to contain an optimized amount of calibration fluid for the pH sensor.

The packaging may be transparent or translucent.

The invention also provides an activation system for an ingestible capsule comprising an ingestible capsule, a magnetic capsule activation unit (21) having an activation port (60), packaging for the capsule, the packaging comprising an open well having an inner surface and an outer surface (54-57), the inner surface configured to engage at least a portion of the ingestible capsule, the outer surface configured for seating in the activation port of the magnetic activation unit, whereby the capsule may be activated without removing the capsule from the packaging.

The activation unit and the packaging may comprising markings (62, 38) indicating a relative alignment for activating the capsule. The activation unit and the packaging may further comprise markings (61, 38) indicating a relative alignment for deactivating the capsule.

The packaging may further comprise a molded engagement surface (52, 53) extending from the well and having a general contour complimentary to at least a portion of an outer surface (63) of the activation unit adjacent the activation port. The molded engagement surface may comprise a planar surface (53) intersecting with an edge of the well and extending perpendicular to the well, and may further comprise a lateral support surface (52) extending generally perpendicular from an outer edge of the planar surface and in the same direction as the well. The outer edge of the planar surface may be generally circular.

The inner surface of the well may be generally cylindrical. The outer surface of the packaging and the activation unit may comprise contours configured to provide a tactile indication when the capsule and outer surface are properly seated in the activation port.

The invention also provides a packaging system for an ingestible capsule comprising an ingestible capsule having a pressure sensor (23), packaging for the capsule comprising an inner surface, the inner surface defining an open well portion (28), the well configured and arranged to engage a first portion (25) of the capsule, and the well, inner surface of the packaging and capsule configured and arranged such that the inner surface of the packaging (74) does not contact the pressure sensor of the capsule when the first portion of the capsule is engaged by the well, whereby the packaging provides for calibrating the pressure sensor without removing the capsule from the packaging.

The well may be configured to engage the first portion of the capsule by being sized such that at least a portion of the capsule fits snuggly into the well, and the well may be configured to receive and releasably hold the capsule by friction. The inner surface of the well may comprise a substantially cylindrical portion, the first portion of the capsule may be substantially cylindrical, and the well portion may have a diameter that is slightly greater than the diameter of the first portion of the capsule.

Accordingly, the general object is to provide an improved packaging system for an ingestible capsule.

Another object is to provide packaging that allows for calibration of a pH sensor on the capsule.

Another object is to provide packaging that does not interfere with calibration of a pressure sensor on the capsule.

Another object is to provide packaging which allows for activation of the capsule with reduced risk of contamination.

Another object is to provide packaging which is adapted to hold calibration fluid.

Another object is to provide packaging which does not contact the pressure sensor on a capsule and thereby interfere with calibration of the pressure sensor.

Another object is to provide packaging that may be opened without undue difficulty.

Another object is to provide packaging that protects the capsule.

Another object is to provide packaging which is adapted to allow for the capsule to be inserted into an activation port.

Another object is to provide packaging with markings that may be used in the activation of the capsule.

Another object is to provide packaging which standardizes and optimizes the volume of calibration fluid used with the capsule.

Another object is to provide a packaging system that allows the capsule to be activated and deactivated without removing the capsule from the packaging.

These and other objects and advantages will become apparent from the foregoing and ongoing written specification, the drawings, and the appended claims.

DESCRIPTION OF THE PREFERRED EMBODIMENTS

Figure 1:
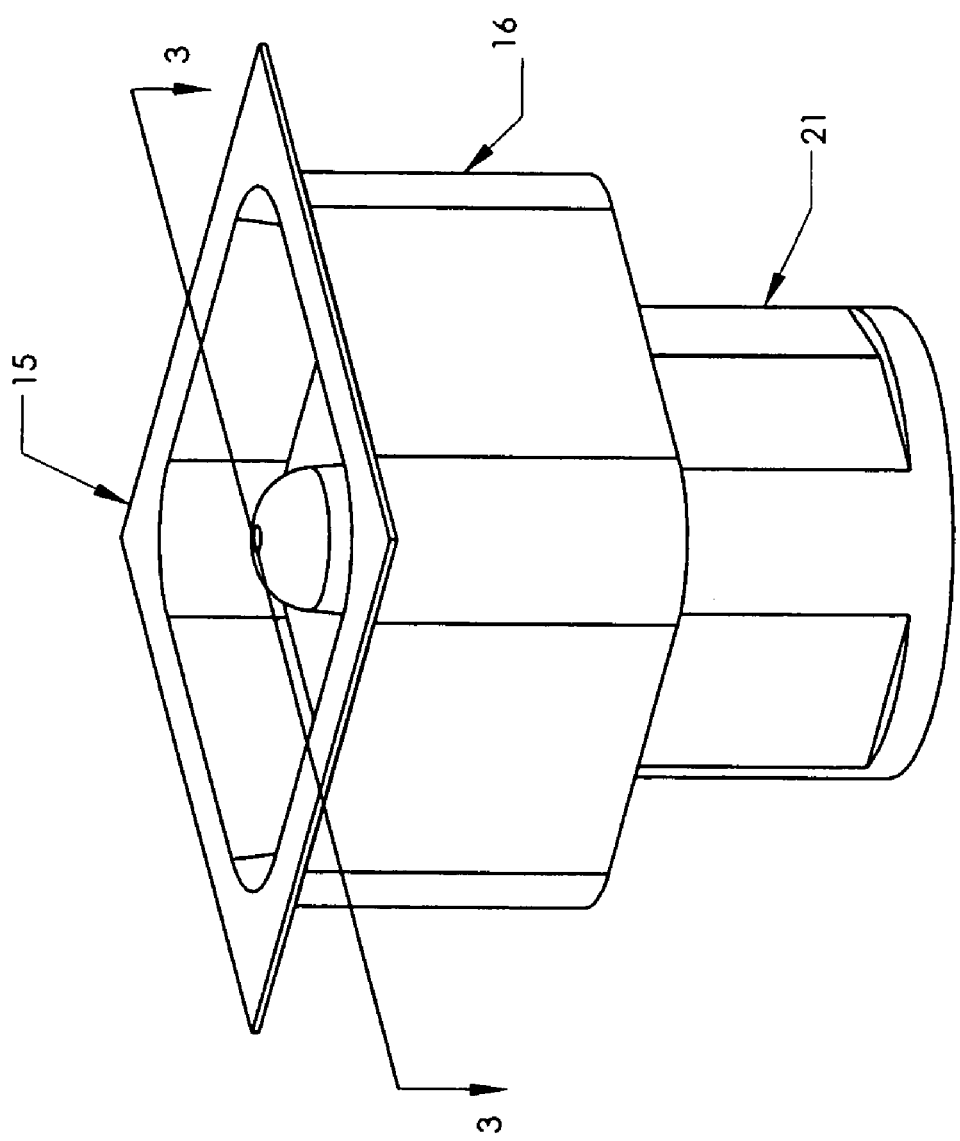
FIG. 1 is a perspective view of the improved packaging together with an ingestible capsule and activation unit.

At the outset, it should be clearly understood that like reference numerals are intended to identify the same structural elements, portions or surfaces, consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 2:
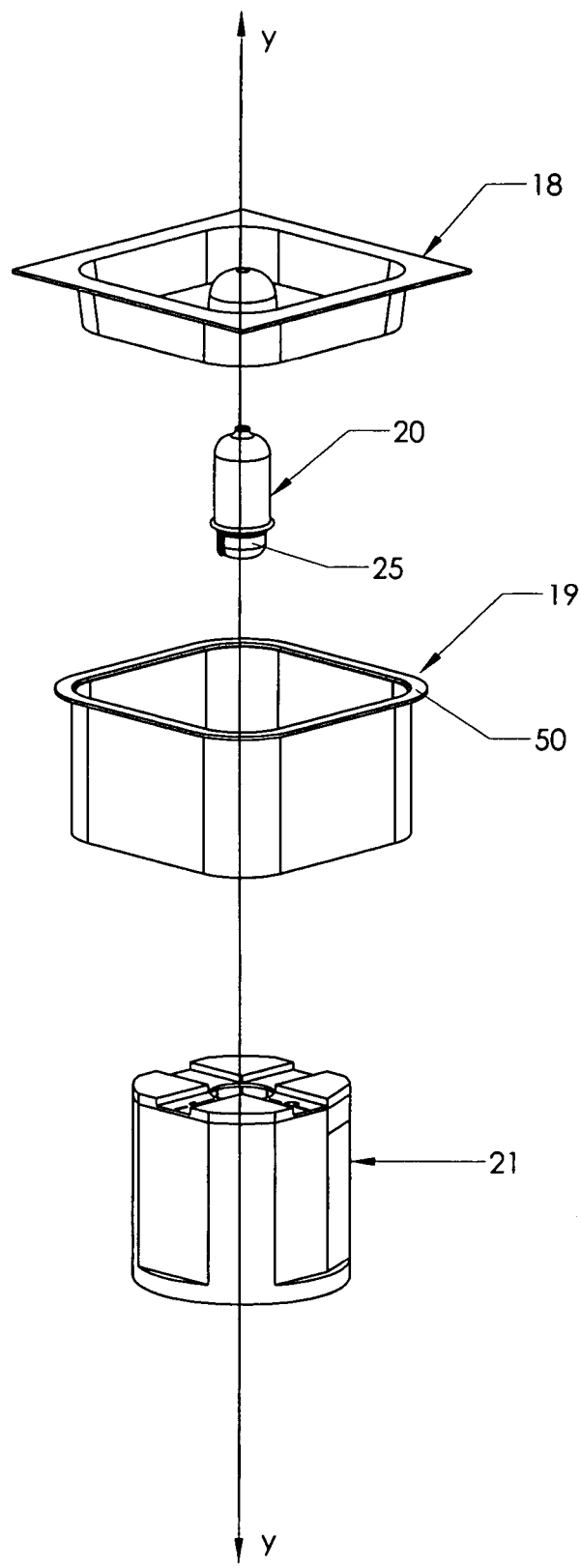
FIG. 2 is an exploded view of the assembly shown in FIG. 1.
Figure 3:
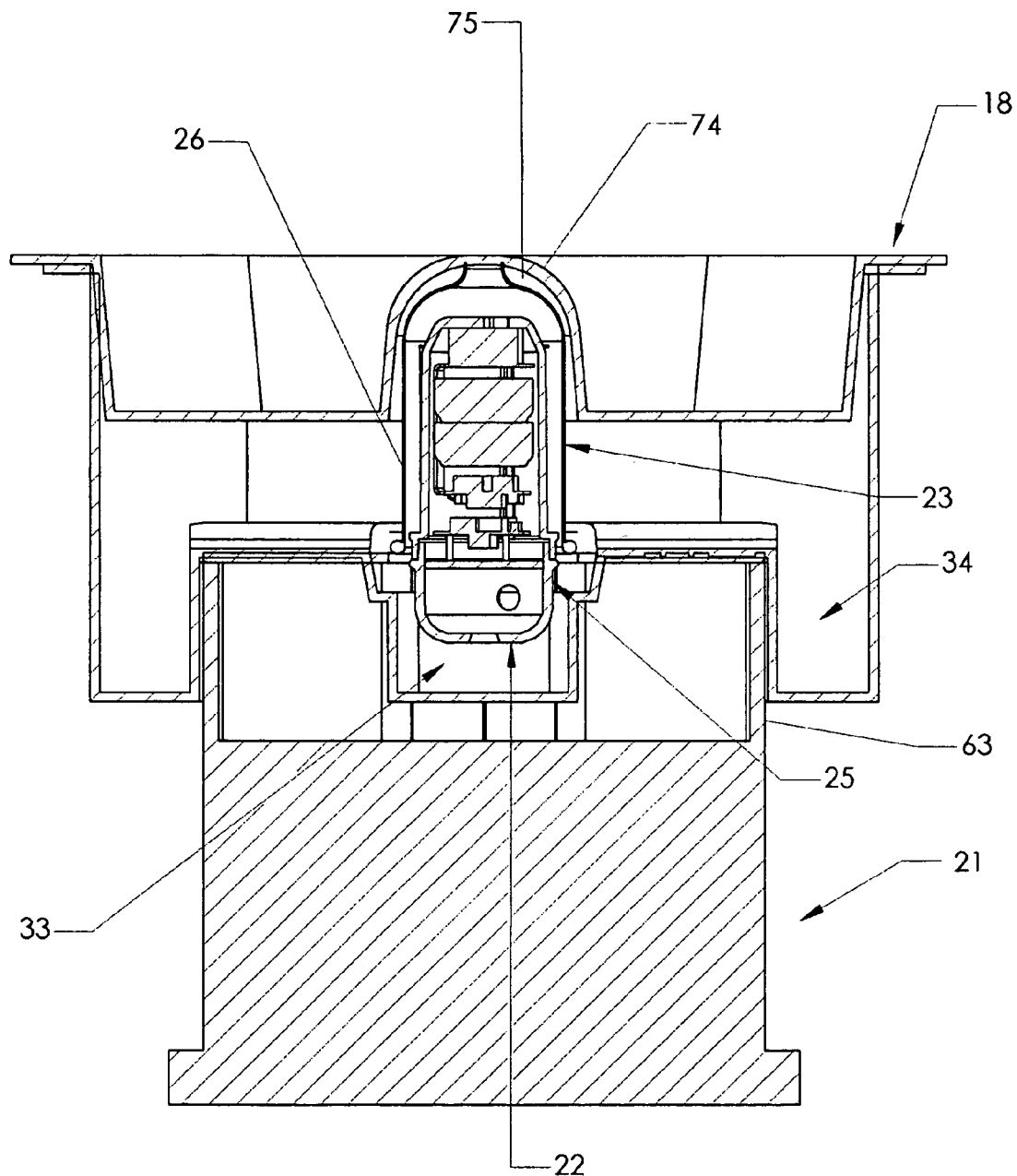
FIG. 3 is a vertical sectional view of the assembly shown in FIG. 1, taken generally on line 3-3 of FIG. 1.
Figure 4:
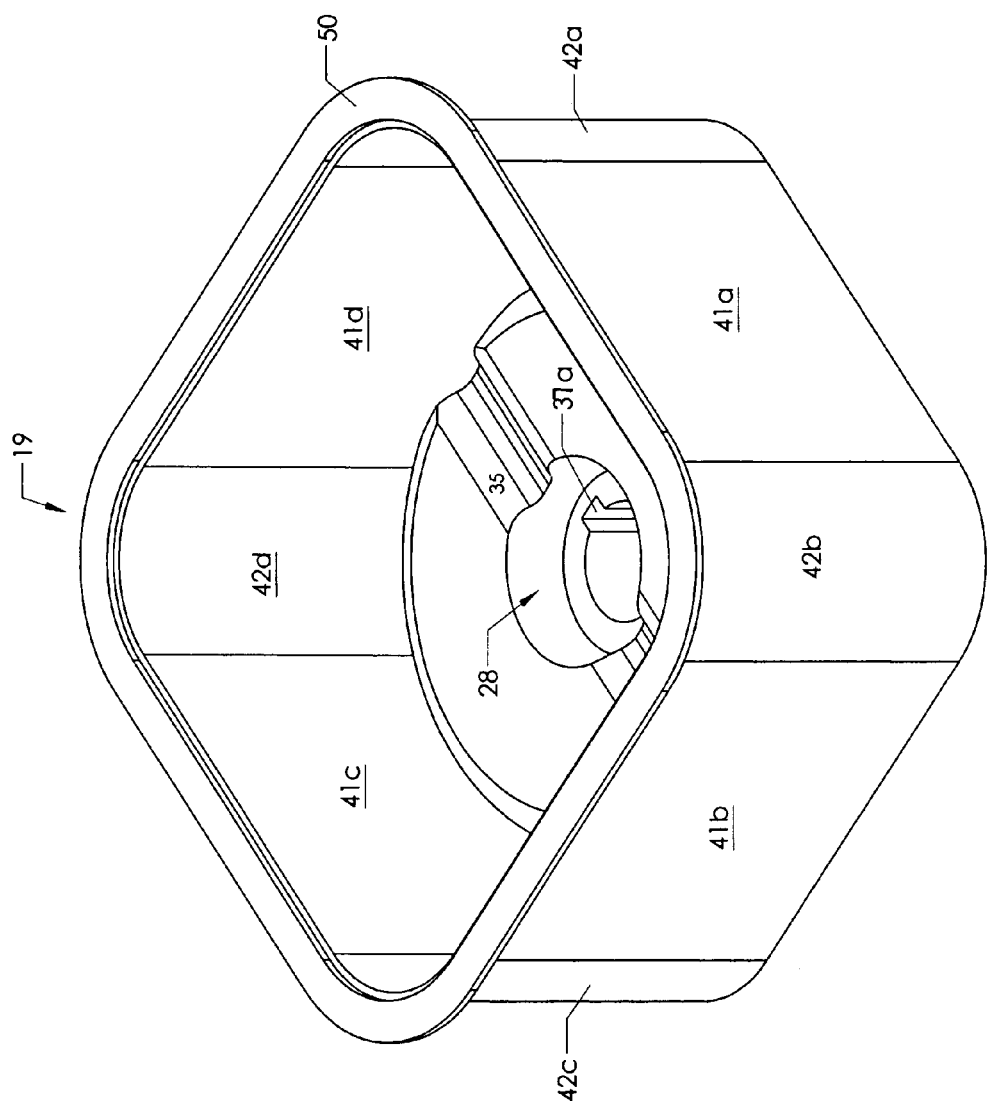
FIG. 4 is a perspective view of the bottom portion of the packaging shown in FIG. 2.

Referring now to the drawings, and more particularly to FIGS. 1-3 thereof, this invention provides a packaging system, the presently preferred embodiment of which is generally indicated at 15. Packaging system 15 generally includes packaging 16, a capsule 20 contained within the packaging, and a magnetic activation unit 21.

Figure 12:
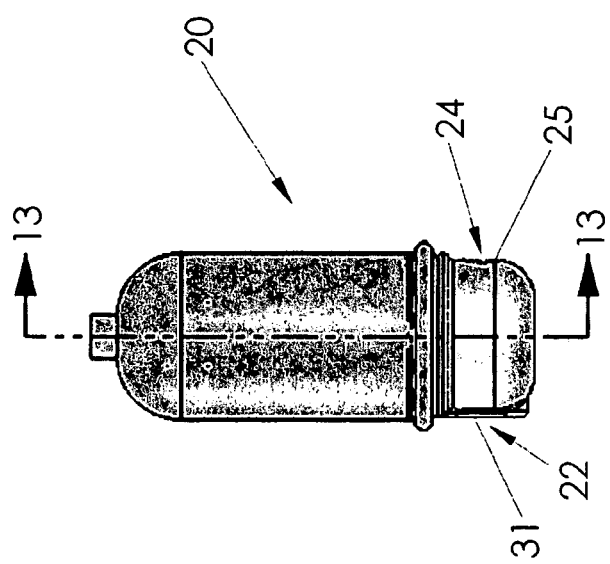
FIG. 12 is a side view of the capsule shown in FIG. 2.
Figure 13:
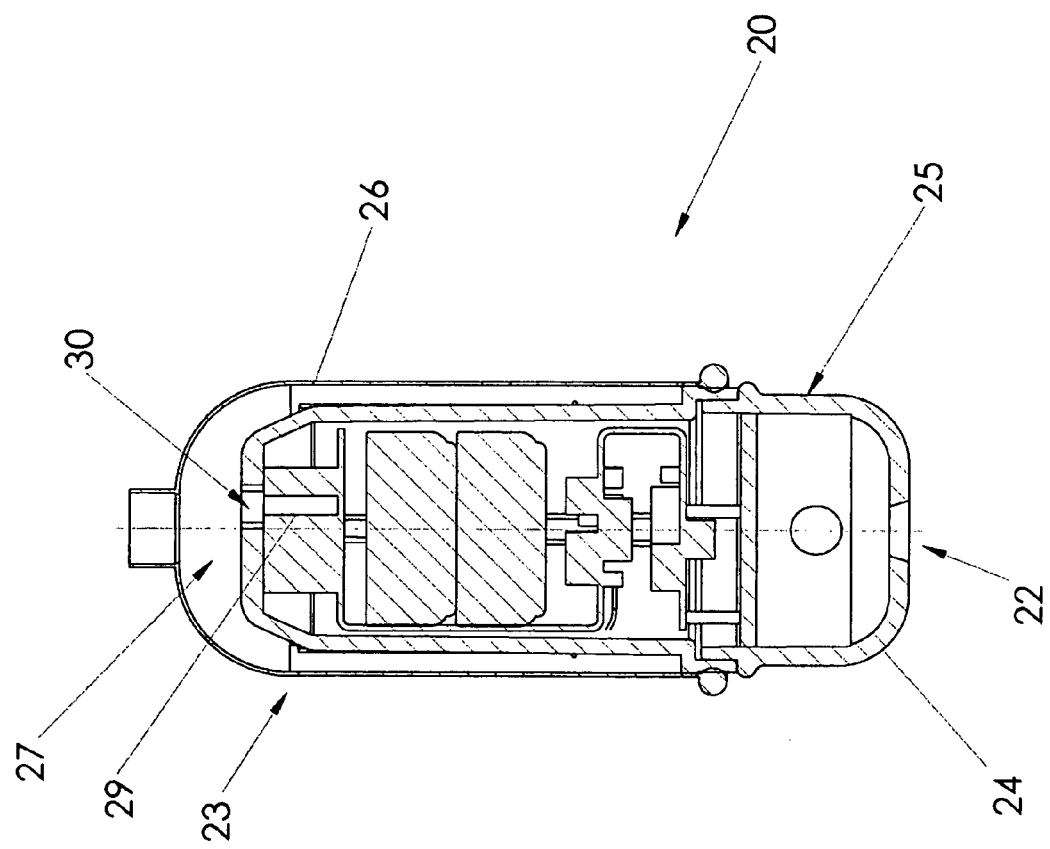
FIG. 13 is a vertical sectional view of the capsule shown in FIG. 12, taken generally on line 13-13 of FIG. 12.

As shown in FIG. 12-13, capsule 20 is an elongated ellipsoid-shaped device, somewhat resembling a medicament capsule. The capsule generally has a hard shell or casing which houses the transmitting electronics, battery compartment and sensors. Capsule 20 is adapted to be ingested, implanted, inserted, or otherwise positioned within a mammalian body or tract to sense both pressure and pH within the body or tract and to transmit such readings. As shown, capsule 20 is generally a cylindrical member elongated about axis y-y and having generally rounded closed ends. The capsule is generally provided with an outer surface to facilitate easy swallowing of the capsule.

Capsule 20 includes a pressure sensor assembly 23 comprising a flexible sleeve 26 affixed to the shell of the capsule and defining a chamber 27 between the shell and the sleeve. A pressure sensor 29 is operatively arranged to sense pressure within chamber 27 and communicates with the chamber through a fluid port 30 at one end of the shell of the capsule.

As shown, the pressure sleeve 26 of capsule 20 extends from a point slightly below the middle of the capsule up over the top end of the capsule. The other end of the capsule is a hard shell 25 which does not interact with the pressure sensor.

On the opposite end of capsule 20 to pressure sensor 23 is a pH sensor 22. In the preferred embodiment, pH sensor 22 is a conventional ISFET type pH sensor. ISFET stands for ion-selective field effect transistor and the sensor is derived from MOSFET technology (metal oxide screen field effect transistor). A current between a source and a drain is controlled by a gate voltage. The gate is composed of a special chemical layer which is sensitive to free hydrogen ions (pH). Versions of this layer have been developed using aluminum oxide, silicium nitride and tantalum oxide. Free hydrogen ions influence the voltage between the gate and the source. The effect on the drain current is based solely on electrostatic effects, so the hydrogen ions do not need to migrate through the pH sensitive layer. This allows equilibrium, and thus pH measurement, to be achieved in a matter of seconds. The sensor is an entirely solid state sensor, unlike glass bulb sensors which require a bulb filled with buffer solution. Only the gate surface is exposed to the sample. Sensor 22, like glass bulb and other electronic pH sensors, must be calibrated before each use.

Capsule 20 includes a small battery that runs the electronics. In order to conserve energy, the capsule is packaged in a deactivated state. Therefore, before use, the capsule must be activated. In the preferred embodiment, activation of the capsule is provided magnetically using a passive magnetic latch, as disclosed in U.S. Publication No. 2006/0114086, entitled "Passive Magnetic Switch", published Jun. 1, 2006, the entire disclosure of which is incorporated herein by reference. The capsule includes a biasing magnet and a magnetically-actuated switch with a component that, when polarized, causes the switch to transition from a first state (open) to a second state (closed). To activate the capsule, it must be placed in close proximity to a suitable external magnetic field in a proper orientation to change the direction of the biasing magnetic field and thereby close the switch and form electrical contact with the battery. In the preferred embodiment, a magnetic activation unit 21 is provided to be used in activating capsule 20. The activation unit includes an activation port 20. When the capsule is placed in the proper alignment within activation port 60, the capsule is in close proximity to permanent magnets in the activation unit which result in closing the switch and activation of the capsule.

Packaging 16 is provided for capsule 20. Packaging 16 generally provides a hollow shell for protectively enclosing capsule 20. Packaging 16 includes a specially configured top portion 18 which mates with a specially configured bottom portion 19. When top portion 18 is snapped into bottom portion 19, their inner surfaces enclose and protect capsule 20. Top and bottom portion 18 and 19 are also translucent, so the capsule can be seen without opening packaging 16 by separating top portion 18 from bottom portion 19.

Packaging 16 includes a number of features which allow for calibration and activation of capsule 20 without fully removing it from the packaging. The top and bottom portions 18 and 19 are specially configured to provide an open well 28 into which capsule 20 is seated. Well 28 also includes space 33 for receiving calibration fluid such that pH sensor 22 may be calibrated while capsule 20 is seated in well 28. In addition, the inner surface of packaging 16 is configured such that it surrounds but does not contact pressure sensor 23 of capsule 20. This allows pressure sensor 23 to be calibrated without removing the capsule from the packaging.

The bottom portion 19 of packaging 16 includes an additional recess or volume 34 adapted to act as a depository for calibration fluid for pH sensor 22. This fluid is necessary for calibrating the capsules pH sensor 22 prior to use of capsule 20. Top portion 18 is removed and calibration fluid is poured directly into recess 34, from which it is then directed into well 28 and into contact with pH sensor 22. The capsule and packaging are orientated such that pH sensor 22 will be exposed to the calibration fluid poured into packaging recess 34. Accordingly, pH sensor 22 may be calibrated without removing the capsule from the bottom portion 19 of packaging 16.

Capsule 20 is held in a well 28 having not only an inner surface adapted to removably engage the capsule and submerge sensor 22 in calibration fluid when desired, but also having an external surface designed to engage a magnetic activation unit. The shape of the packaging allows for a portion of the package to be inserted into an activation port 60 of a magnetic activation unit 21. This allows the capsule to be placed in close proximity to permanent magnets in activation unit 21. The packaging has a marking 38 and the activation unit includes markings 61 and 62 that allow for capsule 20 to be aligned for activation or deactivation as desired.

With reference to FIGS. 4-7, packaging 16 includes a bottom portion 19 and a top portion 18. As shown, bottom portion 19 is generally a unitary molded polygonal body having four side walls 41a-41d and rounded corners 42a-42d.

Figure 6:
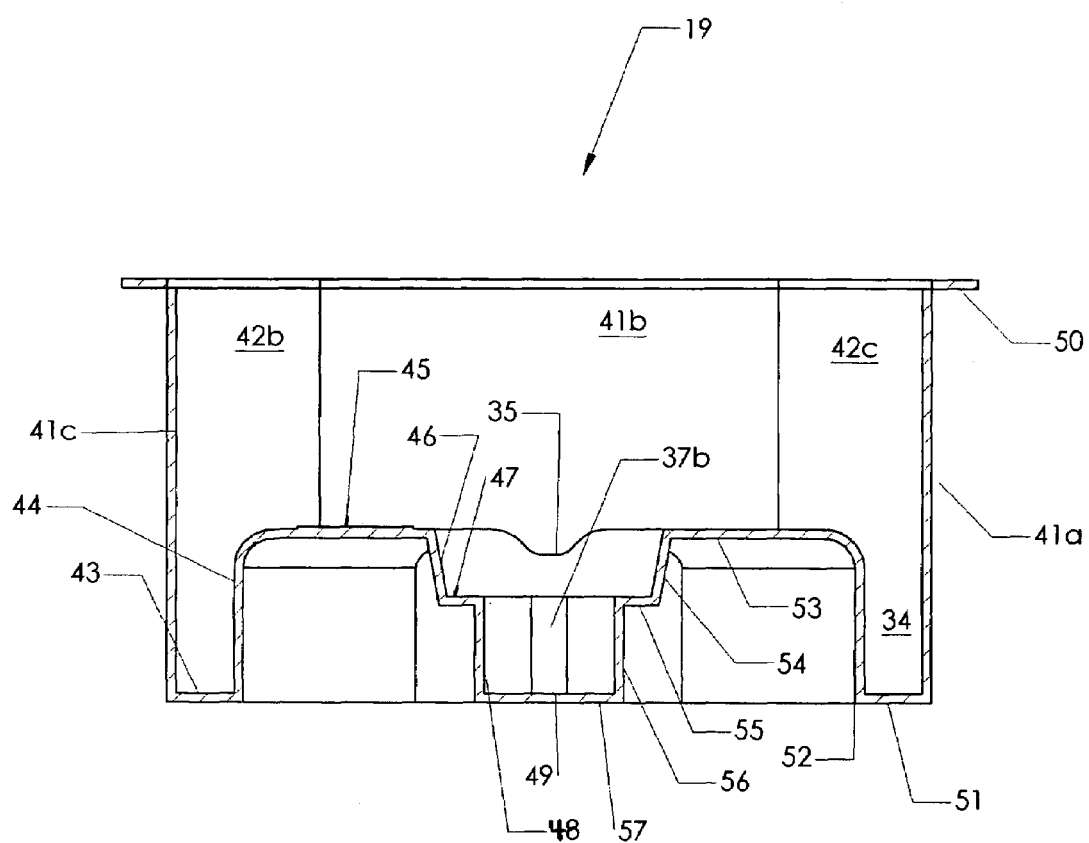
FIG. 6 is a vertical sectional view of the bottom portion of the packaging shown in FIG. 5, taken generally on line 6-6 of FIG. 5.
Figure 7:
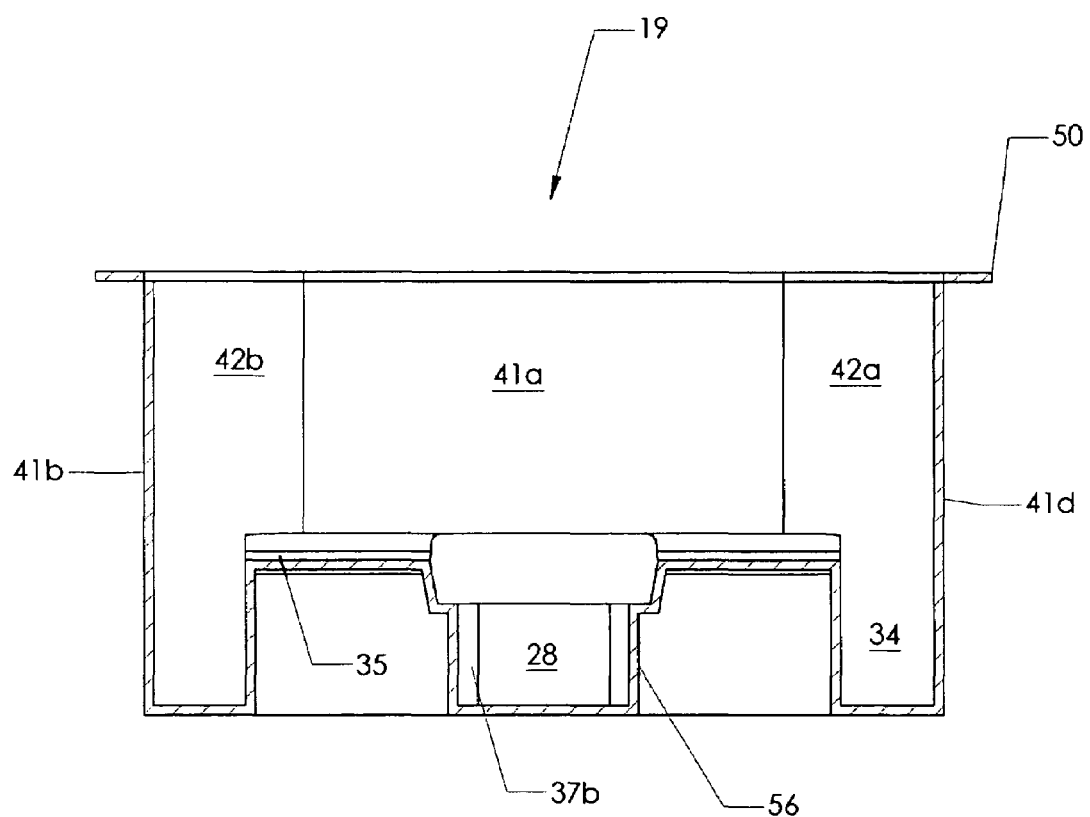
FIG. 7 is a vertical sectional view of the bottom portion of the packaging shown in FIG. 5, taken generally on line 7-7 of FIG. 5.

As shown in FIG. 6, the inner surface of bottom portion 19 is generally bounded by the inwardly-facing vertical surfaces of walls 41a-41d and corners 42a-42d, upwardly-facing annular horizontal surface 43, outwardly-facing vertical cylindrical surface 44, upwardly-facing horizontal annular surface 45, inwardly and upwardly-facing frusto-conical surface 46, upwardly-facing horizontal generally annular surface 47, generally inwardly-facing vertical generally cylindrical surface 48, and upwardly-facing horizontal circular planar surface 49. The top edge of panels 41 and 42 define an opening and include a horizontal abutment lip, rim or flange 50.

As shown in FIG. 6, the outer surface of bottom portion 19 is defined by the outwardly-facing vertical surfaces of outer walls 41a-41d and corners 42a-42d, downwardly-facing horizontal annular surface 51, inwardly-facing vertical cylindrical surface 52, downwardly-facing horizontal annular surface 53, outwardly and downwardly-facing cylindrical frusto-conical surface 54, downwardly-facing horizontal generally annular surface 55, outwardly-facing vertical generally cylindrical surface 56, and downwardly-facing circular planar surface 57.

Figure 5:
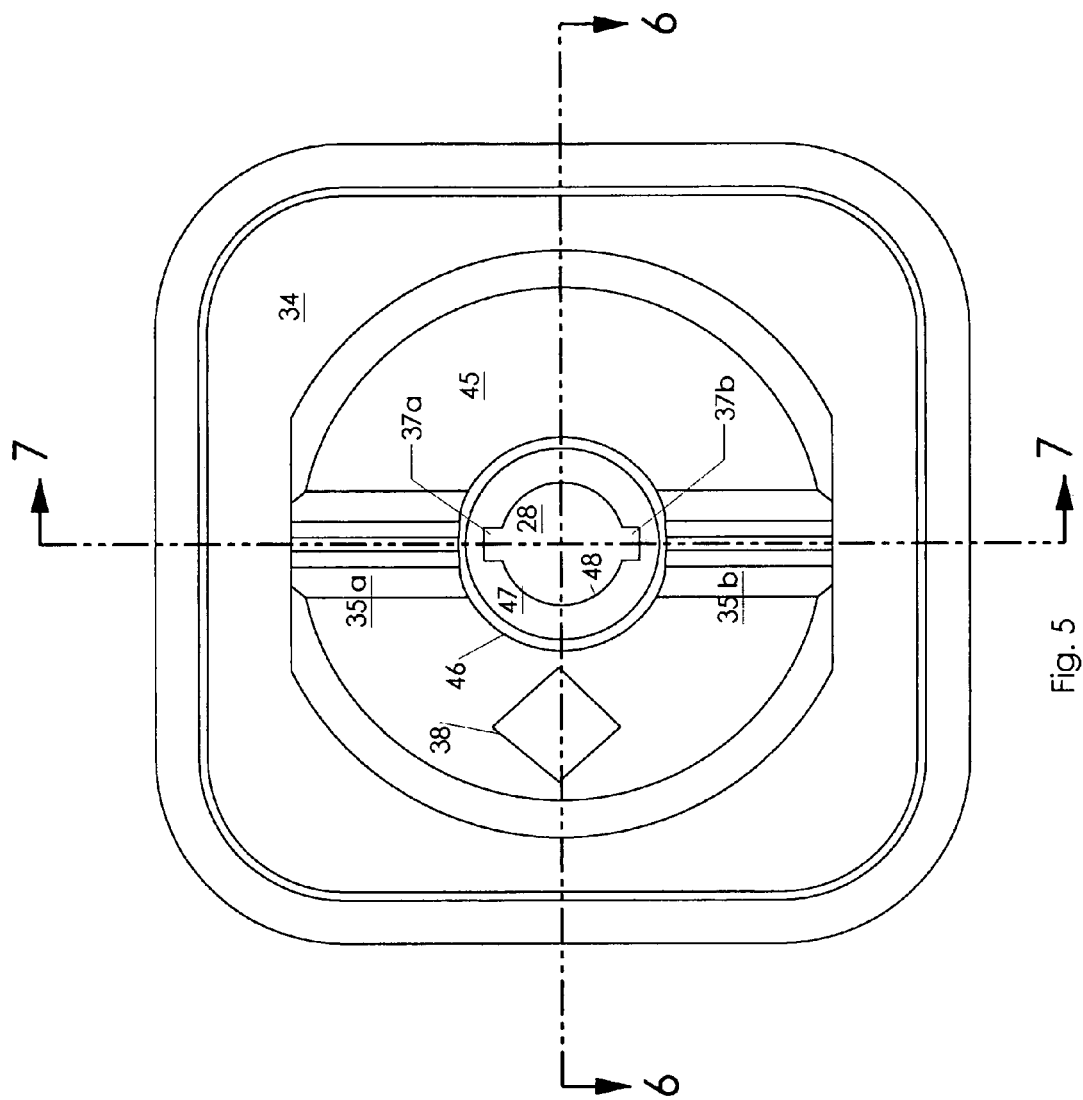
FIG. 5 is top plan view of the bottom portion of the packaging shown in FIG. 4.

As shown in FIGS. 5 and 6, surfaces 46, 47, 48 and 49 define an open well 28 into which the end of capsule 20 is inserted. As shown, the diameter of cylindrical surface 48 is just slightly larger than the diameter of the cylindrical first portion 25 of capsule 20. Thus, inner surfaces 46, 47 and 48 are sized such that first portion 25 of capsule 20 fits snuggly into open well 28. Furthermore, well 28 is sized such that the inner surfaces 46, 47 and 48 of well 28 and the outer bottom surface of capsule 20, as shown in FIG. 3, define a holding or reservoir volume 33. Reservoir 33 is provided to contain and hold pH calibration fluid such that pH sensor 22 of capsule 20 is submerged in such calibration fluid when capsule 20 is seated in well 28 and well 28 is filled with such calibration fluid.

As shown in FIG. 6, bottom portion 19 is provided with both a well 28 and a pouring recess 34. Pouring recess 34 is defined by the lower inner surfaces of walls 41a-d and corners 42a-d, surface 43 and surface 44. Recess 34 and well 28 communicate by way of at least one groove 35 in annular surface 45. Groove 35, as shown in FIG. 5, extends radially from the top inner edge of pouring recess 34 to the top outer edge of well 28. By means of channel 35, calibration fluid may be poured into recess 34 and, once recess 34 has been filed such that the fluid reaches channel 35, is directed by way of channel 35 into well 28 and holding volume 33. Calibration fluid may be provided with packaging 16 in amount such that the overflow from recess 33 that moves through channel 35 into well 28 is optimized to fill well 28 and holding volume 33 such that pH sensor 22 on capsule 20 is submerge. In this way, pH sensor 22 of capsule 20 may be calibrated without having to remove capsule 20 from its seating in bottom portion 19 of packaging 16. Thus, pH sensor 22 may be calibrated without ever having to touch capsule 22.

While inner surfaces 46, 47 and 48 of well 28 are configured to engage capsule 20 by frictional contact, outer surfaces 54, 55, 56 and 57 of well 28 are configured to be seated and fit snuggly into activation port 60 of activation unit 21. Thus, the outer diameter of cylindrical surface 56 is slightly less than the inner diameter of activation port 60. In addition, as shown in FIG. 5, top surface 45 of portion 19 includes a raised mark 38. Also as shown in FIG. 5, cylindrical surface 48 includes two vertically extending opposed notches 37a and 37b. These notches correspond to two longitudinally extending rib elements 31 on the bottom of capsule 20. Thus, capsule 20 must be rotationally aligned such that its longitudinally extending ribs 31 slide into notches 37a and 37b, respectively. Thus, once seated, capsule 20 does not rotate in well 28. Activation unit 21 in turn includes markings 61 and 62. Marking 62 indicates a first position for activating capsule 20 and marking 61 indicates a second position for deactivating capsule 20. With capsule 20 aligned in well 28 of packaging 16, marking 38 may be aligned circumferentially with marking 62, in which case insertion of well 28 into activation port 60 will magnetically activate capsule 20. Alternatively, marking 38 may be aligned with marking 61, in which case insertion of well 28 will magnetically deactivate capsule 20.

The protrusion of grooves 35 below surface 53 provide a means for tactilely knowing when well 28 is properly seated in port 60 of activation unit 21. Grooves 35 have a width that corresponds to the width of bisecting notches 64a-64d of activation unit 21. Thus, when well 28 and packaging 19 are pressed into activation port 60, the protruding outer edges of radial grooves 35 press against the sides of radial notches 64a/64c or 64b/64d, depending on the alignment, such that the user can feel when the capsule is properly and fully seated in activation port 60.

Figure 8:
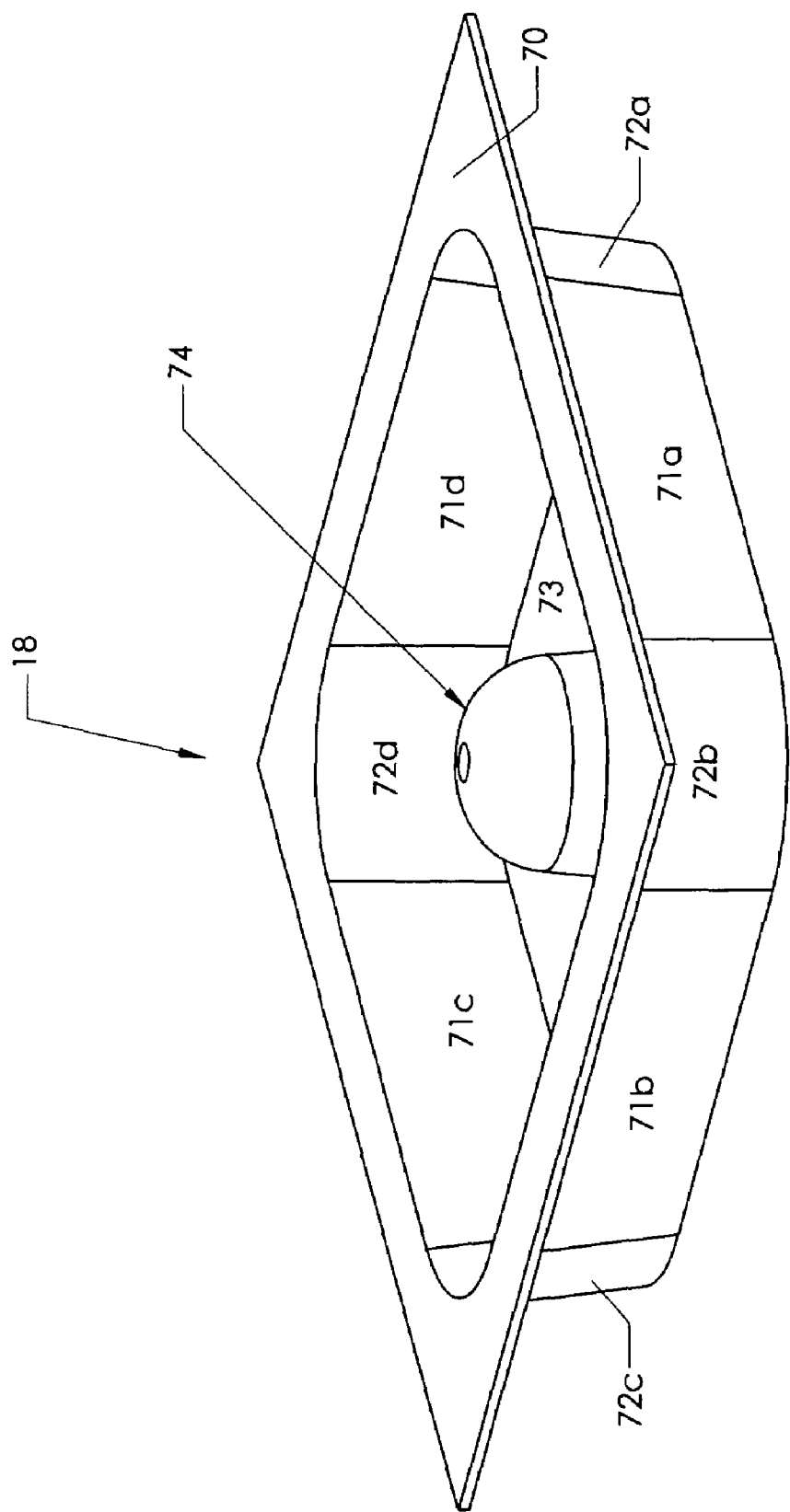
FIG. 8 is a perspective view of the top portion of the packaging shown in FIG. 2.
Figure 9:
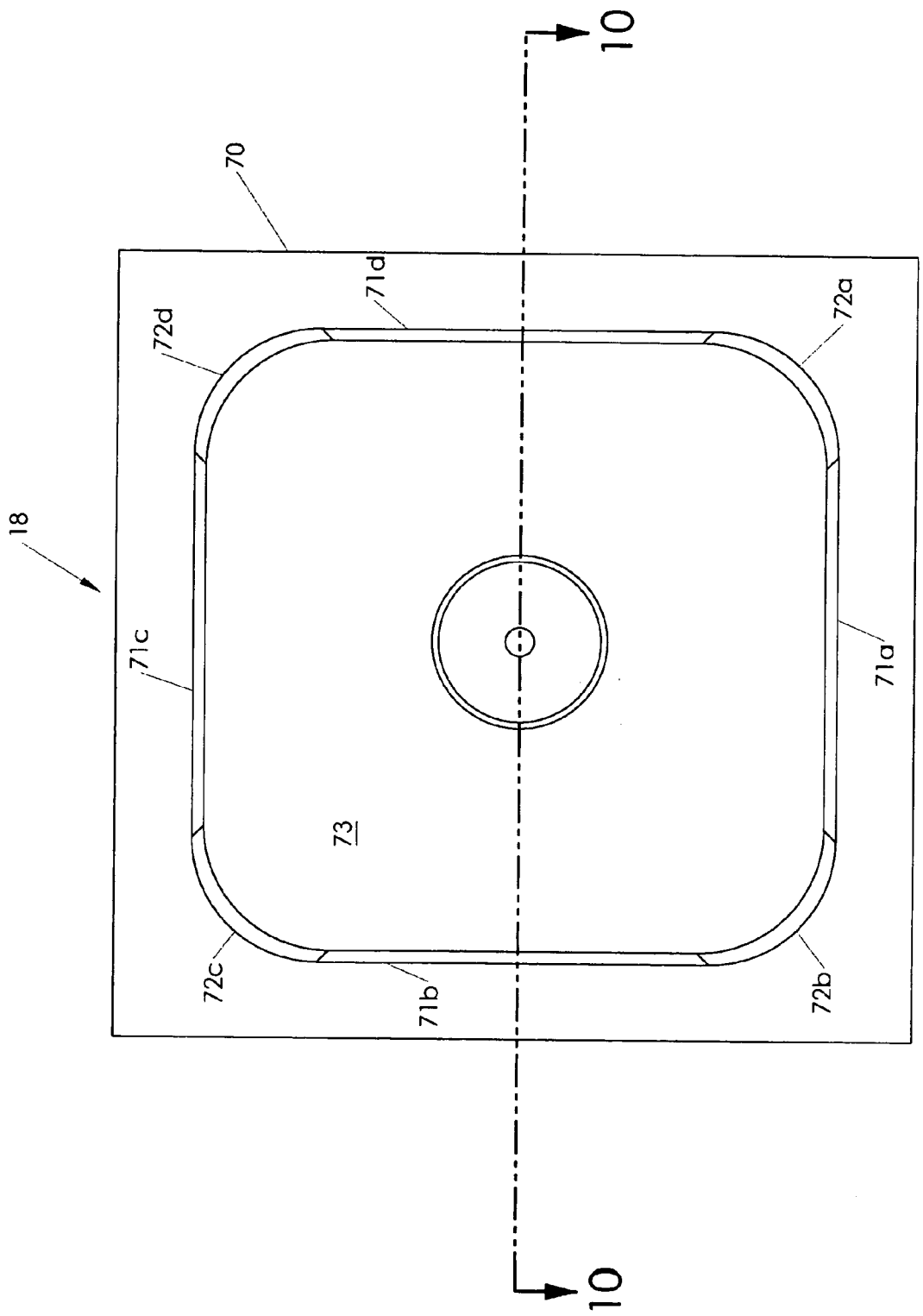
FIG. 9 is a top plan view of the top portion of the packaging shown in FIG. 8.
Figure 10:
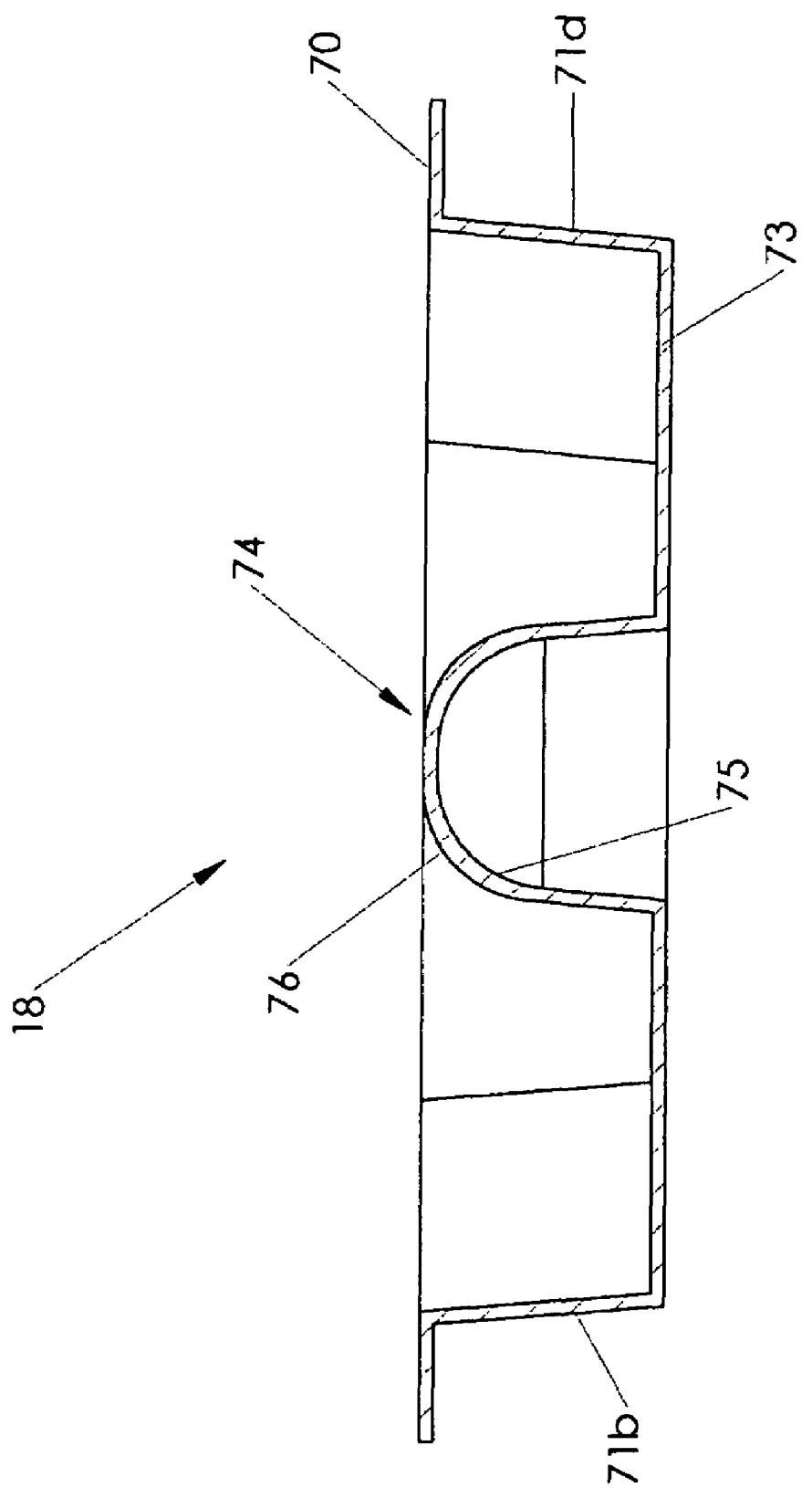
FIG. 10 is a vertical sectional view of the top portion of the packaging shown in FIG. 9, taken generally on line 10-10 of FIG. 9.
Figure 11:
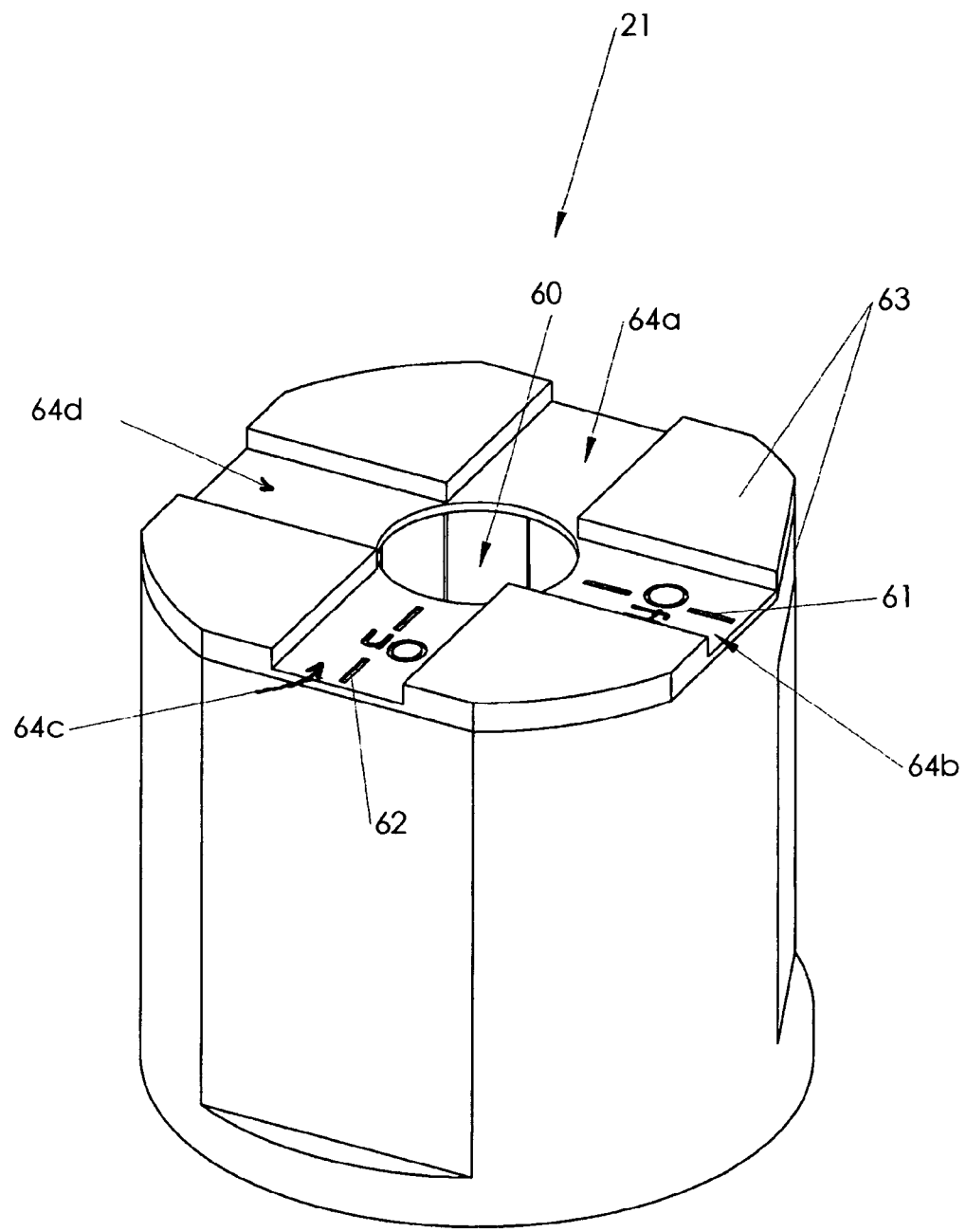
FIG. 11 is a perspective view of the activation unit shown in FIG. 2.

Top portion 18 is an integrally molded transparent body. As shown in FIG. 8, top portion 18 includes a horizontal lip, rim or flange 70. The bottom surface of flange 70 is adapted to abut against the top surface of flange 50 of bottom portion 19. As shown, top portion 18 includes side walls 71a-71d with rounded corners 72a-72d. Sides 71 and corners 72 are dimensioned such that their outside surfaces are slidable within and will contact the inner top surfaces of walls 41 and corners 42 of bottom portion 19. Thus, top portion 18 will extend into the top of bottom portion 19.

Top portion 18 includes a horizontally extending planar top member 73, joined on its outside edge to the bottom edges of walls 71 and corners 72, and joined about an inner circular edge to a domed portion 74. While dome 74 extends above planar portion 73, the top of dome 74 does not extend above the top surface of rim 70. Thus, the top surface of rim 70 provides some protection to the top of dome 74. Dome 74 has an inner surface 74 with contours that correspond to the contour of the outer top surface of capsule 20. However, the inner surface of dome 74 is dimensioned such that it does actually touch the top outer surface of capsule 20 when capsule 20 is properly seated in well 28. The top portion of capsule 20 includes sleeve 26 of pressure sensor 23 of capsule 20 By providing space, as shown in FIG. 3, between the inner surface 75 of dome 74 and the outer top surface of capsule 20, packaging 16 does not exert pressure on pressure sensor 23 of capsule 20. Thus, in its packaging, pressure sensor 23 is calibrated to ambient pressure.

Once capsule 20 is properly seated in well 28, top portion 18 of packaging 16 is pressed onto the top of bottom portion 19. Four horizontal grooves (not shown) in the inner surfaces of each of side walls 41a-41d and corresponding horizontally extending ridges (not shown) on the outside surfaces of each of side walls 71a-71d are provided such that the ridges will fit into the grooves when top portion 18 is properly joined with bottom portion 19. Rim 70 of top portion 18 extends slightly further out at the corners then rim 50 of bottom portion 19. Thus, top portion 18 may be more easily separated from bottom portion 19 by prying the over-extending portion of rim 70 of top portion 18 away from rim 50 of bottom portion 19.

The present invention contemplates that many changes and modifications may be made. Therefore, while the presently preferred form of the packaging system has been shown and described, and several modifications discussed, persons skilled in this art will readily appreciate that various additional changes and modifications may be made without departing from the spirit of the invention, as defined and differentiated by the following claims.

What is claimed is:

1. A packaging system for an ingestible capsule comprising:
   an ingestible capsule having a pH sensor and an outer surface;
   packaging for said capsule comprising an open well having an inner surface and a holding volume defined by said inner surface of said well and said outer surface of said capsule;
   said inner surface of said well configured and arrange to engage at least a portion of said outer surface of said capsule; and
   said holding volume configured and arranged to contain a pH calibration fluid and to hold said pH sensor of said capsule submerged in said pH calibration fluid when said pH calibration fluid is added to said well;
   whereby said packaging provides for calibrating said pH sensor without removing said capsule from said packaging.

2. The packaging system set forth in claim 1, wherein said inner surface is configured to engage at least a portion of said capsule by being sized such that at least a portion of said capsule fits snuggly into said well.

3. The packaging system set forth in claim 1, wherein said inner surface is configured to receive and releasably hold said capsule by friction.

4. The packaging set forth in claim 1, wherein said inner surface of said well comprises a substantially cylindrical portion, said outer surface of said capsule comprises a substantially cylindrical portion, and said well portion has a diameter that is slightly greater than the diameter of said capsule portion.

5. The packaging system set forth in claim 1, and further comprising an open recess configured to receive said calibration fluid and communicating with said well such that calibration fluid poured into said recess is communicated to said holding volume.

6. The packaging set forth in claim 5, wherein said recess and said well communicate by at least one channel between the opening of said recess and the opening of said well.

7. The packaging system set forth in claim 6, wherein said channel is U-shaped.

8. The packaging system set forth in claim 1, wherein said holding volume is configured to contain an optimized amount of calibration fluid for said pH sensor.

9. The packaging system set forth in claim 1, wherein said packaging is transparent or translucent.

10. An activation system for an ingestible capsule comprising:
    an ingestible capsule;
    a magnetic capsule activation unit having an activation port;
    packaging for said capsule;
    said packaging comprising an open well having an inner surface and an outer surface;

said inner surface configured to engage at least a portion of said ingestible capsule;

said outer surface configured for seating in said activation port of said magnetic activation unit;

whereby said capsule may be activated by said activation unit without removing said capsule from said packaging.

11. The activation system set forth in claim 10, wherein said activation unit and said packaging comprise markings indicating a relative alignment for activating said capsule.

12. The activation system set forth in claim 11, wherein said activation unit and said packaging further comprise markings indicate a relative alignment for deactivating said capsule.

13. The activation system set forth in claim 10, wherein said packaging further comprises a molded engagement surface extending from said well and having a general contour complementary to at least a portion of an outer surface of said activation unit adjacent said activation port.

14. The activation system set forth in claim 13, wherein said molded engagement surface comprises a planar surface intersecting with an edge of said well and extending generally perpendicular to said well.

15. The activation system set forth in claim 14, wherein said molded engagement surface further comprises a lateral support surface extending generally perpendicular from an outer edge of said planar surface and in the same direction as said well.

16. The activation system set forth in claim 15, wherein said outer edge of said planar surface is generally circular.

17. The activation system set forth in claim 10, wherein said inner surface of said well is generally cylindrical.

18. The activation system set forth in claim 10, wherein said outer surface of said packaging and said activation unit comprise contours configured to provide a tactile indication when said capsule and outer surface are properly seated in said activation port.

19. A packaging system for an ingestible capsule comprising:

an ingestible capsule having a pressure sensor;

packaging for said capsule comprising an inner surface, said inner surface defining an open well portion;

said well configured and arrange to engage a first portion of said capsule; and said well, said inner surface of said packaging and said capsule configured and arranged such that said inner surface of said packaging does not contact said pressure sensor of said capsule when said first portion of said capsule is engaged by said well;

whereby said packaging provides for calibrating said pressure sensor without removing said capsule from said packaging.

20. The packaging system set forth in claim 19, wherein said well is configured to engage said first portion of said capsule by being sized such that at least a portion of said capsule fits snuggly into said well.

21. The packaging system set forth in claim 19, wherein said well is configured to receive and releasably hold said first portion of said capsule by friction.

22. The packaging set forth in claim 19, wherein said well comprises a substantially cylindrical portion, said first portion of said capsule is substantially cylindrical, and said well portion has a diameter that is slightly greater than the diameter of said first portion of said capsule.

* * * * *